(12) United States Patent
Nicastro et al.

(10) Patent No.: US 10,238,687 B2
(45) Date of Patent: Mar. 26, 2019

(54) METHOD FOR PREPARING A LIPOSOMAL REHYDRATION SALT FORMULATION

(71) Applicant: EINSOF BIOHEALTH LIMITED, Cork (IE)

(72) Inventors: Alcides Nicastro, Santa Fe (AR); Alejandro Luis Barbarini, Santa Fe (AR)

(73) Assignee: EINSOF BIOHEALTH LIMITED, Cork (IE)

( * ) Notice: Subject to any disclaimer, the term of this patent is extended or adjusted under 35 U.S.C. 154(b) by 0 days.

(21) Appl. No.: 15/723,228

(22) Filed: Oct. 3, 2017

(65) Prior Publication Data

US 2018/0028561 A1     Feb. 1, 2018

Related U.S. Application Data

(63) Continuation of application No. 15/111,485, filed as application No. PCT/ES2015/070003 on Jan. 7, 2015.

(30) Foreign Application Priority Data

Jan. 14, 2014 (AR) ............................ P20140100123

(51) Int. Cl.
| | |
|---|---|
| *A61K 9/127* | (2006.01) |
| *A61K 47/02* | (2006.01) |
| *A61K 33/14* | (2006.01) |
| *A23L 2/74* | (2006.01) |
| *A61K 47/22* | (2006.01) |
| *A61K 9/00* | (2006.01) |
| *A23L 2/52* | (2006.01) |

(Continued)

(52) U.S. Cl.
CPC ............... *A61K 33/14* (2013.01); *A23L 2/52* (2013.01); *A23L 2/74* (2013.01); *A61K 9/0095* (2013.01); *A61K 9/127* (2013.01); *A61K 47/12* (2013.01); *A61K 47/22* (2013.01); *A61K 47/26* (2013.01); *A23V 2002/00* (2013.01)

(58) Field of Classification Search
CPC ..................................................... A61K 9/127
See application file for complete search history.

(56) References Cited

U.S. PATENT DOCUMENTS

| | | | |
|---|---|---|---|
| 7,901,708 B2 | 3/2011 | MacLachlan et al. | |
| 2002/0150981 A1* | 10/2002 | Canfield | ............... C07K 16/40 435/69.1 |

(Continued)

FOREIGN PATENT DOCUMENTS

| | | |
|---|---|---|
| WO | 2004002453 | 1/2004 |
| WO | 2015107241 | 7/2015 |

OTHER PUBLICATIONS

Dua et al., "Liposome: Methods of Preparation and Applications," International Journal of Pharmaceutical Studies and Research, vol. III, Issue II, Apr.-Jun. 2012; pp. 14-20.

(Continued)

*Primary Examiner* — Gollamudi Kishore
(74) *Attorney, Agent, or Firm* — Allen, Dyer, Doppelt + Gilchrist, P.A.

(57) ABSTRACT

A liposomal rehydration salt formulation comprising phosphatidylcholine liposomes, salts, water, and a percentage inclusion ratio of salts (salts retained within said liposomes/total salts) of at least 40%; and a process for preparing said formulation using tangential ultrafiltration.

6 Claims, 11 Drawing Sheets

(51) Int. Cl.
  *A61K 47/12* (2006.01)
  *A61K 47/26* (2006.01)

(56) References Cited

U.S. PATENT DOCUMENTS

| | | | |
|---|---|---|---|
| 2005/0008685 A1* | 1/2005 | Mitchell | A23L 2/52 424/450 |
| 2009/0017167 A1 | 1/2009 | Krumhar et al. | |
| 2010/0267806 A1* | 10/2010 | Bumcrot | C12N 15/111 514/44 A |
| 2016/0331778 A1 | 11/2016 | Nicastro et al. | |

OTHER PUBLICATIONS

Crowe et al., "Preservation of Dry Liposomes Does Not Require Retention of Residual Water," Proceedings of the National Academy of Sciences of the United States of America, vol. 84, Mar. 1987; pp. 1537-1540.
Sun et al., "Stability of Dry Liposomes in Sugar Glasses," Biophysical Journal, vol. 70, Apr. 1996; pp. 1769-1776.
About the Asian Conference on Diarrheal Disease and Nutrition (ASCODD) (2012) particularly Bardhan et al., "Clinical Trial of Liposome-Based Oral Rehydration Solution (ORS) in Children with Acute Watery Diarrhoea," at p. 14, PIDSP J., 13 (Suppl.1) pp. 2-23.
Bardhan et al. (2003), "Absorption of Water and Electrolytes from a Liposomal Oral Rehydration Solution: An in Vivo Perfusion Study of Rat Small Intestine," ICDDR,B: Centre for Health and Population Research, GPO Box 128, Dhaka 1000, Bangladesh; 5 pages.
Bardhan et al. (2003), "Absorption of Water and Electrolytes from a Liposomal Oral Rehydration Solution (ORS): An in Vivo Perfusion Study in Rat Small Intestine," PowerPoint Presentation, 13 pages.
Bardhan et al. (2012), "Absorption of Water From a Liposomal Oral Rehydration Solution: An in Vivo Perfusion Study of Rat Small Intestine Exposed to Cholera Toxin," AGA Abstracts, Gastroenterology, 142(5) (Suppl. 1): S-21.
Bardhan et al. (2016), Clinical Trial of Liposome-Based Oral Rehydration Solution (ORS) in Children with Acute Watery Diarrhoea, Powerpoint Presentation, 15 pages.
Bardhan et al. (2016), Liposome-Based Oral Rehydration Solution (ORS) in Children with Acute Watery Diarrhoea: An Exploratory Clinical Trial, 11 pages.
International Search Report and Written Opinion (translation), International Application No. PCT/ES2015/070003, dated Mar. 24, 2015. 17 pages.
Lakougna, H. (2016), "Enteric and Diarrheal Diseases: Landscape Analysis of the Technologies used to Prevent, Diagnose, and Treat Pediatric Cases," Path (NGO), 29 pages.
Pizarro et al. (1991), "Rice-Based Oral Electrolyte Solutions for the Management of Infantile Diarrhea," N. Engl. J. Med. 324:517-521.
Review Proposal Consultation Document (2012), "Review of Clinical Guideline (CG84)—Diarrhoea and Vomiting Caused by Gastroenteritis: Diagnosis, Assessment and Management in Children Younger Than 5 Years," National Institute of Health and Clinical Excellence, 38 pages.
UNICEF/WHO (2001), "New Formulation of Oral Rehydration Salts (ORS) with Reduced Osmolarity," World Health Organization, Dept. of Child and Adolescent Health and Development, Technical Bulletin No. 9; 3 pages.
Wapnir et al. (1988), "Oral Hydration Solutions in Experimental Osmotic Diarrhea: Enhancement by Alanine and Other Amino Acids and Oligopeptides," Am. J. Clin. Nutr., 48:84-90.
Wapnir et al. (1991), "Improved Water and Sodium Absorption from Oral Rehydration Solutions Based on Rice Syrup in a Rat Model of Osmotic Diarrhea," J. Pediatr.118:S53-61.
Faruqui et al., "Perfusion Study on Rat Small Intestine Exposed to Cholera Toxin to Observe Absorption of Water and Electrolytes from a Liposome Based ORS," Journal of Parasitic Diseases: Diagnosis and Therapy, vol. 1, No. 1, 2016; pp. 1-10.
U.S. Appl. No. 15/723,241, filed Oct. 3, 2017.

* cited by examiner

METHOD FOR PREPARING A LIPOSOMAL REHYDRATION SALT FORMULATION

PRIORITY APPLICATION(S)

This is a continuation application of U.S. patent application Ser. No. 15/111,485 filed Jul. 14, 2016, which is based upon a U.S. national stage application as international Application No. PCT/ES2015/070003 filed Jan. 7, 2015, which claims priority from Argentina Patent Application No. P20140100123 filed Jan. 14, 2014, the disclosures which are hereby incorporated by reference in their entirety.

FIELD OF THE INVENTION

The present invention relates to the technological field of improved oral rehydration salts. In particular, it relates to liposomal oral rehydration salts.

STATE OF THE ART

References to oral rehydration salts in the form of liposomes are not abundant in literature. Several attempts to develop isolated products of this kind have been disclosed, which have not been successful.

It should be noted that U.S. Patent Publication No. 2005/0008685 (now abandoned) describes the use of liposomes for preparing oral rehydration salts. However, the percentage inclusion ratio of salts (salts retained within said liposomes/total salts) disclosed is 25%, which in spite of improving mouthfeel, still causes rejection by consumers or patients.

On the other hand, there are several reports on the benefits from administering liposomal rehydration salts, such as in "Absorption of Water and Electrolytes from a Liposomal Oral Rehydration Solution: An in vivo Perfusion Study of Rat Small Intestine" by P. K. Bardhan, A. S. M. Hamidur Rahman, Rifaat, and D. A. Sack—ICDDR, B: Centre for Health and Population Research, GPO Box 128, Dhaka 1000, Bangladesh, published in December 2003. This document makes reference to the improved mouthfeel and improved absorption mechanism of rehydration salts due to the presence of liposomes.

Salt concentration as recommended by the WHO for rehydration salts is the following:

| ORS | | | Concentration mmol/L | | | |
|---|---|---|---|---|---|---|
| Function | Component | g/L | Glucose | Na+ | K+ | Cl- | Cit3- |
| Rehydration salts | Sodium chloride | 2.6 | | 44.5 | | 44.5 | |
| | Potassium Chloride | 1.5 | | | 20.1 | | |
| | Sodium citrate | 2.9 | | 29.6 | | | 9.9 |
| Sweetener | Glucose | 13.5 | 74.9 | | | | |

SUMMARY OF THE INVENTION

Figure 1:
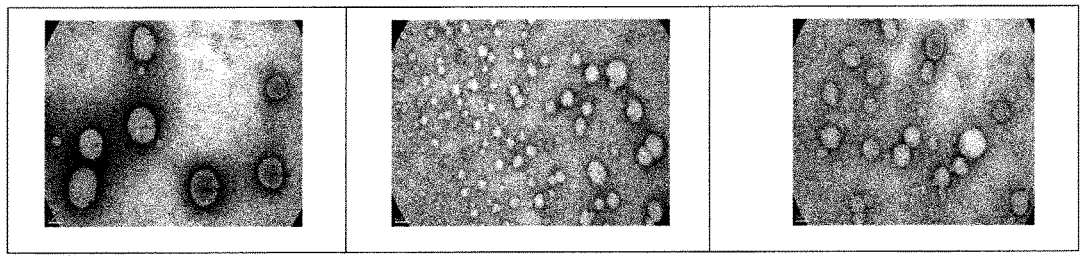
FIG. 1 shows TEM (Transmission Electron Microscopy) images of a liposome sample of the present invention after the final stage of the preparation process.

The present invention provides an improved formulation comprising liposomes that retain more than 40% of total salts, preferably more than 50%, more preferably at least 52%, and even more preferably more than 56%, resulting in a technical effect that solves the main problem actually seen in oral rehydration salts, namely, consumer rejection.

Furthermore, the present invention provides a novel process for the preparation of oral rehydration salt formulations using tangential ultrafiltration, which accounts for indexes of salt retention within the liposomes that have never been disclosed in the literature before. These indexes make it possible to obtain an oral rehydration salt formulation that is pleasant and virtually without any rejection as far as mouthfeel is concerned. Besides, also due to the elevated inclusion of salts within the liposomes, rapid incorporation of the salts into the body is achieved, without the need of high glucose concentrations in the formulation.

The liposomal rehydration salt formulation of the present invention comprises phospholipids that may be selected from phosphatidylcholines (PCs), phosphatidylserines (PSs), phosphatidylethanolamines (PEs), phosphatidylglycerols (PGs), phosphatidylinositols (PIs), phosphatidic acids (PAs), and mixtures thereof, at a concentration of 1 to 60 g/l, preferably 50 g/l; and optionally an antioxidant selected from phytosterol, tocopherol, and mixtures thereof, at a concentration of 0.2 to 0.5% (W/V); water; salts selected from the group consisting of sodium chloride at a concentration of 0.7 to 2.8, preferably from 2.3 to 2.8 g/l, potassium citrate at a concentration of 0.8 to 2.5, preferably from 1.8 to 2.5 g/l, sodium citrate at a concentration of 0.5 to 2.9, preferably from 2.1 to 2.6 g/l, and mixtures thereof. Optionally, it may further comprise carbohydrates. The formulation of this invention comprises a percentage inclusion ratio of salts (salts retained within liposomes/total salts) of at least 40%, preferably at least 50%, more preferably at least 52%, even more preferably at least 56%. In a preferred alternative of the present invention, said percentage inclusion ratio is 56%. The carbohydrates at a concentration of up to 30 g/l, preferably up to 6 g/l, are selected from the group consisting of glucose, fructose, dextrose, high fructose corn syrup, honey, and mixtures thereof, preferably glucose. Furthermore, the formulation of the present invention comprises an osmolality of less than 190 mmol/L.

In addition, the liposomes of the formulation of the invention are produced such that the particle diameter ranges between 200 and 500 nm; preferably between 225 and 450 nm.

The liposomal rehydration salt formulation of the present invention is an oral administration infusion for oral replacement of fluids and electrolyte salts for the treatment of dehydration caused by diarrhea and vomiting, prevention of severe dehydration, and maintenance of body electrolytes and liquids. The present invention may also be an oral administration infusion for use in sport activities.

In a preferred embodiment, the liposomal rehydration salt formulation of the present invention further comprises Stevia at a concentration of 0.1 to 0.2 g/l; sucrose at a concentration of 20 to 50 g/l; citric acid at a concentration of 3 to 4 g/l; and natural flavors at a concentration of 1 to 2 g/l. The formulation is a formulation for rehydration of children.

In another preferred embodiment, the liposomal rehydration salt formulation of the present invention further comprises sucralose at a concentration of 0.1 to 1.5 g/l; high fructose corn syrup (55° Brix) at a concentration of 20 to 50 g/l; citric acid at a concentration of 3 to 5 g/l; and natural flavors at a concentration of 1 to 2 g/l. The formulation comprises a pediatric formula for acute hypotonic dehydration.

In another preferred embodiment, the liposomal rehydration salt formulation of the present invention further comprises Stevia at a concentration of 0.1 to 0.2 g/l; sucrose at a concentration of 20 to 25 g/l; citric acid at a concentration of 3 to 4 g/l; and natural flavors at a concentration of 1 to 2 g/l. The formulation comprises a formulation for rehydration in sport activities.

The process for preparing the formulation of the invention comprises the following steps:
  a. preparing an aqueous phase (AP) or buffer comprising sodium chloride, potassium citrate, sodium citrate dissolved in distilled water;
  b. separately preparing an ethanol phase (EP), by dissolving phospholipids selected from the group consisting of phosphatidylcholines (PCs), phosphatidylserines (PSs), phosphatidylethanolamines (PEs), phosphatidylglycerols (PGs), phosphatidylinositols (PIs), phosphatidic acids (PAs), and mixtures thereof, at a concentration of 0.1 to 6% (W/V), preferably from 2.5 to 5% (W/V); and said antioxidant at a concentration of 0.2 to 0.5% (W/V) in alcohol, preferably ethyl alcohol;
  c. inducing formation of liposomes by injecting said EP into said AP at room temperature, while stirring;
  d. subjecting the liposomal solution obtained in step "c" to a tangential ultrafiltration (TUF) concentration process, removing the buffer and maintaining the liposomes and their contents, thus reducing the volume at least by 10-fold;
  e. subjecting the liposomal solution obtained in step "d" to a tangential ultrafiltration (TUF) concentration process, wherein the ethanol is removed and the buffer is replaced with a saline solution, and maintaining the liposomes and their contents.

In step "a" of the process of the present invention, said aqueous phase (AP) or buffer comprises sodium chloride at a concentration of 6 to 20 mmol/l, preferably from 15 to 20 mmol/l; potassium citrate at a concentration of 1 to 7 mmol/l, preferably from 2 to 7 mmol/l; sodium citrate at a concentration of 2 to 5 mmol/l, preferably from 3 to 5 mmol/l; and distilled water.

In step "e" of the process of the present invention, said saline solution comprises a sodium concentration of 12 to 50 mmol/l, preferably from 20 to 50 mmol/l; a potassium concentration of 3 to 14 mmol/l, preferably from 5 to 14 mmol/l; a chloride concentration of 5 to 40 mmol/l, preferably from 15 to 40 mmol/l; a citrate concentration of 3 to 10 mmol/l, preferably from 5 to 10 mmol/l; and it further comprises glucose at a concentration of 17 to 45 mmol/l, preferably from 35 to 45 mmol/l.

In addition, the volume ratio AP:EP in step "c" is at least 10:3; preferably at least 10:1; preferably at least 10:0.5; more preferably at least 10:0.4.

The process of the present invention comprises a perpendicular flow process, wherein the ethanol phase is added on the aqueous phase by perpendicular coupling to the flow of the former, and with a linear velocity ratio REP/RAP of no more than 1/200.

Another object of the invention is the use of the liposomal rehydration salt formulation, which comprises oral administration to humans suffering from dehydration caused by diarrhea and vomiting.

Another object of the invention is the use of the formulation for human consumption in order to prevent severe dehydration and maintain body electrolytes and liquids.

DETAILED DESCRIPTION

The liposomal rehydration salt formulation of the present invention contains phospholipid liposomes, preferably selected from the group consisting of phosphatidylcholines (PCs), phosphatidylserines (PSs), phosphatidylethanolamines (PEs), phosphatidylglycerols (PGs), phosphatidylinositols (PIs), phosphatidic acids (PAs), and mixtures thereof, at a concentration of less than 6% (W/V); and optionally an antioxidant selected from phytosterol, tocopherol, and mixtures thereof, at a concentration of 0.2 to 0.5% (W/V); water; salts selected from the group consisting of sodium chloride at a concentration of 0.7 to 2.8 g/l, potassium citrate at a concentration of 0.8 to 2.5 g/l, sodium citrate at a concentration of 0.5 to 2.9 g/l, and mixtures thereof; optionally, it may further comprise carbohydrates, among which glucose is preferred.

Intestinal salt absorption mechanisms are enterocyte cotransport systems. These systems involve carrying salts into the body along with other molecules, glucose being the most important among them. This is why rehydration salt formulations targeting hyponatremia, associated both with sports and acute diarrhea, are composed of a mixture of salts and glucose. Salt concentration should be higher than that of the body, so that glucose-mediated transport can be enabled by an osmotic gradient allowing for incorporation of salts through membranes. However, glucose intake is restricted by the calorie intake of this molecule.

Liposomes are nanoparticles consisting of a phospholipid bilayer, the same as cell membranes of enterocytes. Based on different mechanisms, liposomes (and all the contents carried in them) are highly capable of being absorbed by the small intestine cells, increasing bioavailability of the transported actives. Liposomal rehydration salt formulations aim at providing transport mechanisms of liposomes to the basic mechanisms of salts. In vivo tests have shown that an encapsulated ORS formulation having salt concentrations in accordance with WHO standards causes a 1.39-fold hydration increase in animals under normal conditions, as compared to the WHO recommended formula, and a 1.45-fold hydration increase in animals infected with cholera as compared to the WHO recommended formula ("Absorption of Water From a Liposomal Oral Rehydration Solution: an In Vivo Perfusion Study of Rat Small Intestine Exposed to Cholera Toxin" Gastroenterology—Volume 142, Issue 5, Supplement 1, Pages S-21, May 2012—Pradip K. Bardhan, Nasirul Islam, Rifat Faruqui).

In view of the above, one of the great advantages of the present invention relies on the use of lower carbohydrate concentrations, ranging from 0 to 6 g/l, which improves mouthfeel and tolerance to the formulation. Furthermore, it would be possible to replace glucose with a mixture of carbohydrates such as fructose, dextrose, high fructose corn syrup and mixtures thereof, and even with artificial sweeteners such as sucralose. Low glucose concentration is very important in sport drinks. It is even possible to accomplish efficient rehydration in the absence of glucose, which would allow the formulation to be consumed by diabetics.

In addition, and also due to lower glucose concentration, the formulation of the present invention exhibits reduced osmolality with respect to commercially-available formulations, also lower than 190 mmol/L, which accounts for the possibility of accomplishing efficient rehydration without running the risk of inducing hypernatremia in the patient.

Furthermore, one of the novel aspects of this invention is the fact that it significantly improves percentage inclusion ratio of salts (salts retained within said liposomes/total salts) with respect to the prior art. This ratio is at least 40%, preferably at least 50%, more preferably at least 52%. In a preferred alternative of the present invention, said percentage inclusion ratio is at least 56%. These inclusion ratio values have not been previously disclosed in the prior art, and they allow for the preparation of formulations containing lower salt concentrations with improved rehydration effects, as disclosed in the present invention. This inclusion ratio is achieved by using tangential ultrafiltration method. Although well-known, this method has never been employed to increase the ratio of oral rehydration salts encapsulated within liposomes to the total amount of the salts of the formulation, thereby solving the technical problem of rejection caused by oral rehydration salts due to their unpleasant taste.

It has been demonstrated in Example 4 that encapsulation of more than 50% of the salts in the formulation of the present invention causes unpleasant taste inherent to salts to be almost imperceptible. This facilitates consumption by children younger than 12 years, who represent the most affected population in terms of acute dehydration.

Figure 2:
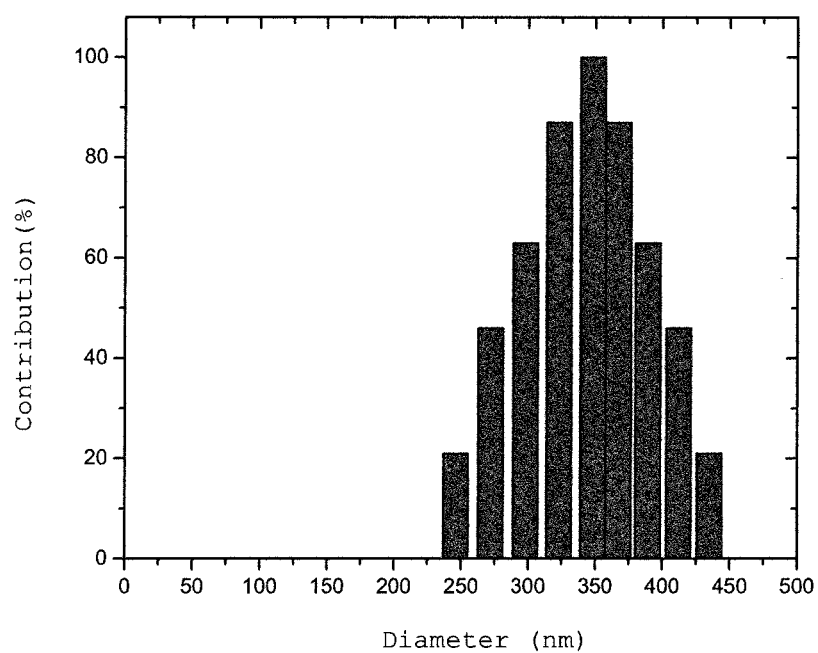
FIG. 2 illustrates the diameter distribution of the liposomes of the present invention formulation, wherein the particle size distribution in a DLS (Dynamic Light Scattering) analysis is shown.

Furthermore, the liposomes of the formulation of the invention are produced such that the particle diameter ranges from 200 to 500 nm; preferably from 225 to 450 nm, as shown in FIG. 2.

The liposomal rehydration salt formulation of the present invention is an oral administration infusion for oral replacement of fluids and electrolyte salts in the treatment of dehydration caused by diarrhea and vomiting, prevention of severe dehydration, and maintenance of body electrolytes and liquids. The present invention may also be an oral administration infusion for use in sport activities.

The process for preparing the formulation of the invention comprises the following steps:

a. preparing an aqueous phase (AP) or buffer comprising sodium chloride, potassium citrate, sodium citrate dissolved in distilled water;

b. separately preparing an ethanol phase (EP), by dissolving said phospholipid at a concentration of 0.1 to 6% (W/V), and optionally an antioxidant at a concentration of 0.2 to 0.5% (W/V) in alcohol, preferably ethyl alcohol;

c. inducing formation of liposomes by injecting said EP into said AP at room temperature, while stirring;

d. subjecting the liposomal solution obtained in step "c" to a tangential ultrafiltration (TUF) concentration process, removing the buffer and maintaining the liposomes and their contents, thus reducing the volume at least by 10-fold;

e. subjecting the liposomal solution obtained in step "d" to a tangential ultrafiltration (TUF) concentration process, wherein ethanol is eliminated and the buffer is replaced with saline solution, and maintaining the liposomes and their contents.

In step "a", said aqueous phase (AP) or buffer comprises sodium chloride at a concentration of 6 to 20 mmol/l, potassium citrate at a concentration of 1 to 12 mmol/l, sodium citrate at a concentration of 2 to 5 mmol/l, and distilled water.

In step "e" of the process of the present invention, said saline solution comprises a sodium concentration of 12 to 50 mmol/l, a potassium concentration of 3 to 36 mmol/l, a chloride concentration of 15 to 40 mmol/l, a citrate concentration of 8 to 17 mmol/l, and it further comprises glucose at a concentration of 17 to 45 mmol/l.

Furthermore, the AP:EP volume ratio in step "c" is at least 10:1; preferably at least 10:0.5; more preferably at least 10:0.4.

The process of the present invention comprises a perpendicular flow process, wherein the ethanol phase is added on the aqueous phase by perpendicular coupling to the flow of the former, and with a linear velocity ratio REP/RAP of no more than 1/200.

EXAMPLES

Example 1

Preparation of the Liposomal Rehydration Salt Formulation of the Invention a) Preparation of the Ethanol Phase (EP)

25 g of purified soybean phosphatidylcholine and 0.5 L of ethanol are added, heated to 65° C., and stirred until completely dissolved. A total amount of 2.5 g of mixed tocopherols (ascorbyl palmitate and D-Alpha-Tocopherol) is added as antioxidant. The solution is left to rest until it reaches room temperature.

b) Preparation of the Saline Aqueous Phase (AP)

4.33 g Sodium chloride, 3.42 g Potassium citrate, and 4.83 g Sodium citrate are dissolved in 4.5 L water and stirred at room temperature until completely dissolved.

c) Production of Liposomes 0.5 L of Ethanol phase is slowly added on 4.5 L of Aqueous phase under continuous circular stirring. This may be also performed by means of a Cross-Flow or Perpendicular Flow process, wherein the Ethanol phase is added on the Aqueous phase by perpendicular coupling to the flow of the former, and with a linear velocity ratio, REP/RAP, of no more than 1/200. FIG. 1 shows liposomes formed with both processes. FIG. 2 shows the results of particle size distribution in DLS (Dynamic Light Scattering) analysis.

d) Increasing Encapsulation Efficiency

Ultrafiltration without recirculation, by tangential flow, is carried out so as to remove the aqueous phase solutes that are not trapped in the liposomes. This process is completed after removing 90% volume of the previous liposomal dispersion.

e) Buffer Substitution

Ultrafiltration by tangential flow is carried out to remove ethanol from the liposomal salt solution. While the process is conducted, the solution is fed at a speed equal to the permeation speed with an aqueous solution of Sodium chloride (1.05 mg/ml), Potassium citrate (0.83 mg/ml), Sodium citrate (1.17 mg/ml) and Glucose (6.75 mg/ml).

The liposomal rehydration salt formulation of the present invention is thereby obtained, said formulation having the following features:

Percentage inclusion ratio of salts (salts retained within liposomes/total salts) of 56.48%

Chloride concentration: 39.7 mmol/L

Citrate concentration: 16 mmol/L

Potassium concentration: 17.9 mmol/L

Sodium concentration: 69.7 mmol/L

Glucose concentration: 33.0 mmol/L

Example 2

Process for Preparing the Present Invention Formulation with a Percentage Inclusion Ratio of Salts of 56%

Stage a

A solution of 4.5 L distilled water with salts is prepared at the following concentration:

|  | Concentration (mmol/L) | | | | |
| --- | --- | --- | --- | --- | --- |
|  | Glucose | Na | K | Cl | Cit |
| Sodium chloride |  | 14.82 |  | 14.82 |  |
| Potassium citrate |  |  | 6.70 |  | 2.23 |
| Sodium citrate |  | 11.23 |  |  | 3.74 |
| Glucose | — |  |  |  |  |

Stage b

Separately, a solution of Phosphatidylcholine in 500 ml of 5% ethyl alcohol (W/V) is prepared.

Stage c

Formation of liposomes is induced by injecting the ethanol solution into the aqueous phase while stirring. Then 15% of the salts are encapsulated; therefore, internal and external salt concentrations are as follows:

|  | Internal | External |
| --- | --- | --- |
| Na | 3.91 | 22.14 |
| K | 1.00 | 5.70 |
| Cl | 2.23 | 12.60 |
| Cit | 0.895 | 5.074 |
| Glucose | 0 | 0 |

Stage d

Five (5) liters of liposomal ORSs are subjected to a tangential ultrafiltration concentration process. This process allows for removing the buffer without eliminating the liposomes and their contents. This process is performed until the volume is reduced by 10-fold. At the end of the process, 500 ml of liposomal salts having the following concentration is obtained.

|  | Internal | External |
| --- | --- | --- |
| Na | 39.1 | 22.14 |
| K | 10.0 | 5.70 |
| Cl | 22.3 | 12.60 |
| Cit | 8.95 | 5.074 |
| Glucose | 0 | 0 |

Stage e

At this stage, the buffer is substituted by using the TUF process again. In this case, the total volume is reduced by 10-fold, and replaced with an aqueous solution with the following salt concentration.

|  | Concentration (mmol/L) |
| --- | --- |
| Na | 31.57 |
| K | 8.13 |
| Cl | 17.96 |
| Cit | 7.24 |
| Glucose | 40.70 |

Accordingly, 500 ml of a solution of liposomal ORSs having the following salt concentration is obtained.

|  | Internal | External | TOTAL |
| --- | --- | --- | --- |
| Na | 39.1 | 30.64 | 69.74 |
| K | 10.0 | 7.88 | 17.88 |
| Cl | 22.3 | 17.45 | 39.75 |
| Cit | 8.95 | 7.02 | 15.97 |
| Glucose | 0 | 33.03 | 33.03 |

The so obtained formulation exhibits a salt concentration equal to that of the formulation recommended by the WHO, with an encapsulation efficiency of about 56.05%. Other features recommended by the WHO and UNICEF in their joint statement issued in May 2004 and accomplished in this invention are reduced glucose content and lower osmolality.

The liposomal rehydration salt formulation of the present invention is thereby obtained, said formulation having the following features:

Percentage inclusion ratio of salts (salts retained within liposomes/total salts) of 56.05%

Chloride Concentration: 39.75 mmol/l

Citrate Concentration: 15.97 mmol/l

Potassium Concentration: 17.88 mmol/l

Sodium Concentration: 69.74 mmol/l

Glucose Concentration: 33.03 mmol/l

Example 3

Encapsulation Efficiency Using the Barium Sulphate Turbidity Method

Two phosphatidylcholine ethanol solutions are prepared, one of them named "FE1", which has a concentration of 2% Phosphatidylcholine (the same as the one used in the TLEC formulation of U.S. Patent Publication No. 2005/0008685), and the other named "FE2", with a concentration of 5% Phosphatidylcholine (the same as the one used in the present invention).

Separately, an aqueous solution (AP) of 56.23 mM ammonium sulphate is prepared (this concentration reproduces the ionic strength of the WHO rehydration salts).

Two liposomal solutions are then prepared using the ethanol phase injection method, in which 10 ml FE1 and FE2 are separately injected in two fractions of 90 ml AP under magnetic stirring at 300 rpm and 25° C. Consequently, 100 ml of two liposomal formulations are obtained:

1:10 (v/v) FE1:AP (LIPO-1)
1:10 (v/v) FE2:AP (LIPO-2)

The LIPO-2 formulation was subjected to a tangential ultrafiltration process using a hollow fiber cartridge with a 300 KD cut off, without feedback. Ultrafiltration continued until reducing the volume by 10-fold. This is the process we carry out in our invention in order to obtain higher encapsulation efficiency.

Samples are taken from both final solutions.

Then, 10 ml of each formulation (LIPO-1 and LIPO-2) is taken and ultrafiltered by using the same system but feeding back each formulation with 126 mM sucrose aqueous buffer. Thus, the sulphate ions non-encapsulated into liposomes are eliminated from each solution and substituted with a solution having the same osmolality in order to ensure integrity of the liposomal membranes.

Then 5 ml of each formulation is taken before and after the ultrafiltration process, and 10% surfactant Triton X-100 is added to each of them, in order to break the lipid membranes. This solution is kept under stirring at 25° C. for 1 hour.

Turbidity Measurement

Soluble sulphates precipitate in the presence of barium chloride in the form of barium sulphate ($BaSO_4$) as a white solid. Measurement of tance reduction as a consequence of the presence of barium sulphate, to a certain wave length in a UV/Vis spectrometer allows for determination of the sulphate ion concentration in aqueous solution.

Figure 3:
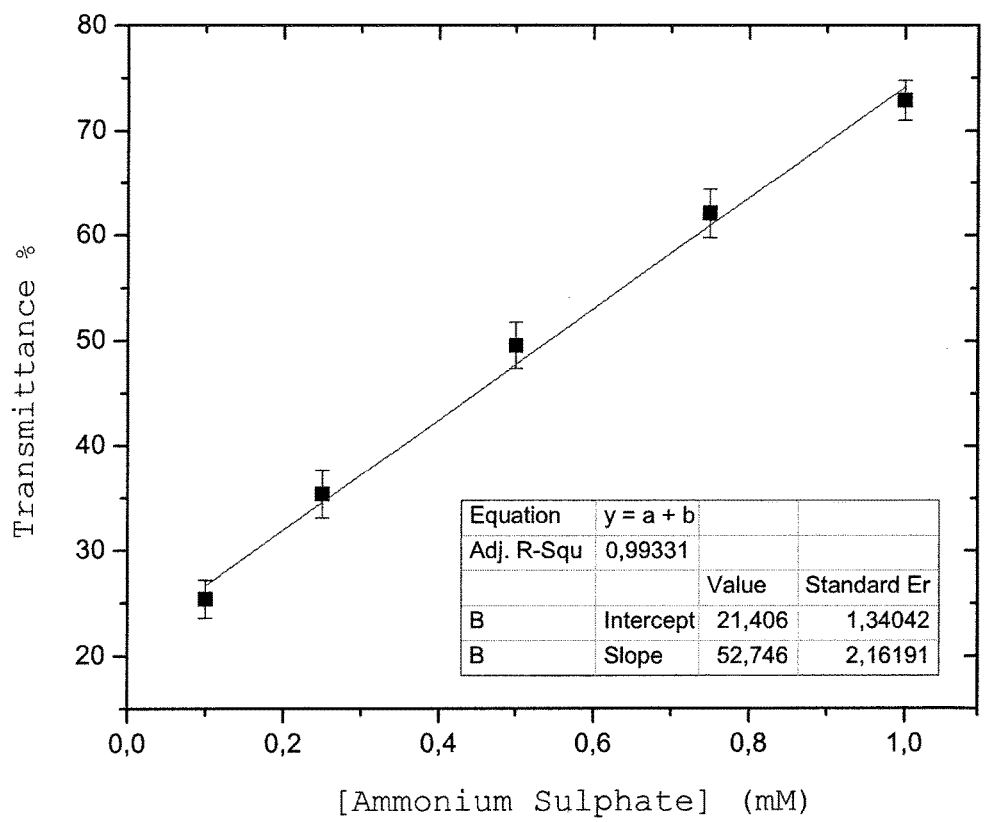
FIG. 3 illustrates a calibration curve for turbidity measurement.

For experimental determination, a calibration curve was plotted by using 50 ml ammonium sulphate patterns with the following concentrations: 0.1 mM, 0.25 mM, 0.5 mM, 0.75 mM and 1 mM. An excess of 31.23 mg (3 mM) barium chloride was added to each solution. Then, transmittance of each solution was determined in triplicate by using an UV/VIS spectrometer (Jenway 7315). The calibration curve is shown in FIG. 3.

Then, 0.1 ml of the unknown LIPO-1 solution before ultrafiltration and 1 ml of the solution after ultrafiltration were taken, both already treated with surfactant, and the same excess of barium chloride was added (3 mM). Transmittance of the sample before ultrafiltration was 49.22%±0.17%, corresponding to [Sulphate]=0.5273 mM. Taking dilutions into account, the total sulphate concentration before ultrafiltration is 52.73 mM. Transmittance of the sample after ultrafiltration was 48.25%±0.32%, corresponding to [Sulphate]=0.5091 mM. Taking dilutions into account, the salt concentration after ultrafiltration is 5.091 mM. This indicates that the ratio of sulphate encapsulated in the formulation produced with the concentration of Phosphatidylcholine of U.S. Patent Publication No. 2005/0008685 was 10.59%.

Likewise, 0.1 ml of the unknown LIPO-2 solution before ultrafiltration, and 0.1 ml of the solution after ultrafiltration were taken, both already treated with surfactant, and the same excess of barium chloride was added (3 mM). Transmittance of the sample before ultrafiltration was 73.19%±0.19%, corresponding to [Sulphate]=0.9818 mM. Taking dilutions into account, the total sulphate concentration before ultrafiltration is 98.18 mM. Transmittance of the sample after ultrafiltration was 50.66%±0.24%, corresponding to [Sulphate]=0.5545 mM. Taking dilutions into account, the salt concentration after ultrafiltration is 55.45 mM. This indicates that the ratio of sulphate encapsulated in the formulation of the present invention was 56.48%.

Note: The results are directly proportional to the encapsulated rehydration salts, since all the salts have similar and increased water solubility. Therefore, the encapsulation level by the method of liposome formation by ethanol phase injection is statistical, and it will be similar in compounds with similar water solubility.

Example 4

Multicenter, Randomized and Single-Blind Mouthfeel Assay

Liposomal Rehydration Salts
Samples:

Formula A: Liposomal rehydration salt formulation of example 3 of the present invention.

Formula B: Liposomal rehydration salts according to example 3 of U.S. Patent Publication No. 2005/0008685 A1.

Methodology

Healthy individuals from 21 to 40 years of age were recruited. Those individuals with cardiac or renal diseases, diabetics, individuals who had suffered from diarrhea the month prior to the assay, individuals affected by rhinitis, or individuals under antibiotic or iron treatment were excluded from the assay.

The screening of the individuals took place in four different shopping malls in the city of Santa Fe, Argentina. After explaining the test to the individuals and having them signed their consent (either by themselves or by their parents or legal guardians in case of underage people), the individuals were randomized. Randomization indicates the order in which the two formulations would be tasted. In order to get familiar with this type of flavors, the individuals took a little sip of the two formulations and then rinsed their mouths with water and a piece of salt-free bread. Thereafter, they tasted the two formulations in the order indicated by randomization, and they were asked to indicate the formulation of their preference. The same test was repeated twice with both formulations, after a new mouth rinse with water and pieces of bread. They were offered each formulation in amounts of less than 20 ml in total, inside red plastic glasses (to avoid color influence on the decision). The formulations were administered at room temperature, without any refrigeration.

Each individual tasted both formulations repeatedly (twice the first tasting and twice the second tasting); to corroborate consistency both times each tasting took place, kappa(k) statistic was used (URL: www.graphpad.com/quickcalcs/kappa2.cfm) as well as a 95% CI.

Results 120 individual were studied, out of which 4 individuals did not meet the inclusion criteria (out of age), so the final test cohort consisted of 116 individuals with an average of 30-32 years old. The distribution of the individuals per shopping mall was similar: between 27 and 30 per each shopping mall. 59 individuals were female (50.9%).

Regarding the results obtained, we found very high consistency between the scores of the 2 tests with the same formulations, both in the first tasting (k=0.91; 95% CI: 0.85-0.98), and the second tasting (k=0.87; 95% CI: 0.80-0.94). Therefore, in the statistical analysis, it was decided to use the results corresponding to the second time each of the two tastings was scored.

Out of the 116 individuals, 97 individuals preferred the taste of formula A, 2 preferred the taste of formula B. 17 individuals were not certain as to which they preferred, so they were not counted.

Example 5

Process for Preparing the Formulation of the Present Invention with a Percentage Inclusion Ratio of Salts of 56% (for Sport Activities)

Stage a

A solution of 4.5 L distilled water is prepared with salts at the following concentration:

| | Concentration (mmol/L) | | | | |
|---|---|---|---|---|---|
| | Glucose | Na | K | Cl | Cit |
| Sodium chloride | | 6.01 | | 6.01 | |
| Potassium citrate | | | 3.86 | | 1.29 |
| Sodium citrate | | 6.02 | | | 2.01 |
| Glucose | — | | | | |

Stage b

On the other hand, a solution of phosphatidylethanolamine in 500 ml of 4% Ethyl Alcohol (W/V) is prepared.

Stage c

Liposome formation is induced by injecting the ethanol solution into the aqueous phase while stirring. Here, 15% of the salts are encapsulated. Therefore, the internal and external salt concentrations are the following:

| | Internal | External |
|---|---|---|
| Na | 1.57 | 10.46 |
| K | 0.50 | 3.36 |
| Cl | 0.78 | 5.23 |
| Cit | 0.49 | 2.81 |
| Glucose | 0 | 0 |

Stage d

The Five (5) liters of liposomal ORSs are subjected to a tangential ultrafiltration (TUF) concentration process. This process allows for removing the buffer without eliminating the liposomes and their contents. This process is carried out until reducing the volume by 10-fold. At the end of the process, 500 ml liposomal salts having the following concentration are obtained.

| | Internal | External |
|---|---|---|
| Na | 15.7 | 10.56 |
| K | 5.04 | 3.46 |
| Cl | 7.84 | 5.23 |
| Cit | 4.90 | 2.81 |
| Glucose | 0 | 0 |

Stage e

At this stage, buffer substitution is performed, again with the TUF process. In this case, the total volume is reduced by 10-fold and replaced with an aqueous solution having the following salt concentration:

| | Concentration (mmol/L) |
|---|---|
| Na | 12.56 |
| K | 3.65 |
| Cl | 5.65 |
| Cit | 3.04 |
| Glucose | 17.80 |

This buffer further contains Stevia (Reb A 97—PureCircle) at a concentration of 0.15 g/L; Sucrose at a concentration of 28.5 g/L; Citric Acid at a concentration of 3.6 g/L; and Natural Flavors at a concentration of 1.5 g/L.

Accordingly, 500 ml of a liposomal ORS solution is obtained, containing 40 g/l phospholipid, with the following salt concentration:

| | Internal | External | TOTAL |
|---|---|---|---|
| Na | 15.7 | 12.35 | 28.05 |
| K | 5.04 | 3.62 | 8.66 |
| Cl | 7.84 | 5.61 | 13.45 |
| Cit | 4.90 | 3.02 | 7.92 |
| Glucose | 0 | 16.02 | 16.02 |

The formulation of the present example is useful for people in need of hydration due to sun exposure, illness, pregnancy, travel fatigue, hangover, mental stress, strenuous work, or just living an active life. It may be produced with orange, strawberry, apple, pear, blueberry, raspberry flavors, among others.

Example 6

Process for Preparing the Formulation of the Present Invention with a Percentage Inclusion Ratio of Salts of 56%

Pediatric Rehydration Formulation.

Stage a

A solution of 4.5 L distilled water is prepared with salts at the following concentration:

| | Concentration (mmol/L) | | | | |
|---|---|---|---|---|---|
| | Glucose | Na | K | Cl | Cit |
| Sodium chloride | | 14.82 | | 14.82 | |
| Potassium citrate | | | 6.70 | | 2.23 |
| Sodium citrate | | 11.23 | | | 3.74 |
| Glucose | — | | | | |

Stage b

On the other hand, a solution of phosphatidylserine in 500 ml of 3% Ethyl alcohol (W/V) is prepared.

Stage c

Liposome formation is induced by injecting the ethanol solution into the aqueous phase while stirring. Here, 15% of the salts are encapsulated. Therefore, the internal and external salt concentrations are the following:

| | Internal | External |
|---|---|---|
| Na | 3.91 | 22.14 |
| K | 1.00 | 5.70 |

-continued

|  | Internal | External |
|---|---|---|
| Cl | 2.23 | 12.60 |
| Cit | 0.895 | 5.074 |
| Glucose | 0 | 0 |

Stage d

The Five (5) liters of Liposomal ORSs are subjected to a tangential ultrafiltration concentration process. This process allows for removing the buffer without eliminating the liposomes and their contents. This process is carried out until the volume is reduced by 10-fold. At the end of the process 500 ml of liposomal salts having the following concentration is obtained.

|  | Internal | External |
|---|---|---|
| Na | 39.1 | 22.14 |
| K | 10.0 | 5.70 |
| Cl | 22.3 | 12.60 |
| Cit | 8.95 | 5.074 |
| Glucose | 0 | 0 |

Stage e

At this stage, buffer substitution is carried out, again with the TUF process. In this case, the total volume is reduced by 10-fold and replaced with an aqueous solution having the following salt concentration:

|  | Concentration (mmol/L) |
|---|---|
| Na | 31.57 |
| K | 8.13 |
| Cl | 17.96 |
| Cit | 7.24 |
| Glucose | 40.70 |

This buffer further contains Sucralose at a concentration of 0.12 g/L; high fructose corn syrup (55° Brix) at a concentration of 33.3 g/L; Citric Acid at a concentration of 4.0 g/L; and Natural Flavors at a concentration of 1.7 g/L.

Accordingly, 500 ml of a liposomal ORS solution with 30 g/l phosphatidylserine and the following salt concentration is obtained:

|  | Internal | External | TOTAL |
|---|---|---|---|
| Na | 39.1 | 30.64 | 69.74 |
| K | 10.0 | 7.88 | 17.88 |
| Cl | 22.3 | 17.45 | 39.75 |
| Cit | 8.95 | 7.02 | 15.97 |
| Glucose | 0 | 33.03 | 33.03 |

The formulation of the present example is useful for children suffering from vomiting or diarrhea under the risk of dehydration, and it may be produced with orange, strawberry, apple, pear, blueberry, raspberry flavors, among others.

Example 7

Process for Preparing the Formulation of the Present Invention with a Percentage Inclusion Ratio of Salts of 56%

Stage a

A solution of 4.5 L distilled water is prepared with salts at the following concentration:

|  | Concentration (mmol/L) | | | | |
|---|---|---|---|---|---|
|  | Glucose | Na | K | Cl | Cit |
| Sodium chloride |  | 6.01 |  | 6.01 |  |
| Potassium citrate |  |  | 3.86 |  | 1.29 |
| Sodium citrate |  | 6.02 |  |  | 2.01 |
| Glucose | — |  |  |  |  |

Stage b

On the other hand, a solution of Phosphatidylcholine in 500 ml of 5% Ethyl alcohol (W/V) is prepared.

Stage c

Liposome formation is induced by injecting the ethanol solution into the aqueous phase while stirring. Here, 15% of the salts are encapsulated. Therefore, the internal and external salt concentrations are the following:

|  | Internal | External |
|---|---|---|
| Na | 1.57 | 10.46 |
| K | 0.50 | 3.36 |
| Cl | 0.78 | 5.23 |
| Cit | 0.49 | 2.81 |
| Glucose | 0 | 0 |

Stage d

The five (5) liters of Liposomal ORSs are subjected to a tangential ultrafiltration concentration process. This process allows for removing the buffer without eliminating the liposomes and their contents. This process is carried out until the volume is reduced by 10-fold. At the end of the process, 500 ml of liposomal salts having the following concentration is obtained.

|  | Internal | External |
|---|---|---|
| Na | 15.7 | 10.46 |
| K | 5.04 | 3.46 |
| Cl | 7.84 | 5.23 |
| Cit | 4.90 | 2.81 |
| Glucose | 0 | 0 |

Stage e

At this stage, buffer substitution is carried out, again with the TUF process. In this case, the total volume is reduced by 10-fold and replaced with an aqueous solution having the following salt concentration:

|  | Concentration (mmol/L) |
|---|---|
| Na | 12.56 |
| K | 3.65 |
| Cl | 5.65 |

-continued

| | Concentration (mmol/L) |
|---|---|
| Cit | 3.04 |
| Glucose | 17.80 |

This buffer further contains *Stevia* (Reb A 97—PureCircle) at a concentration of 0.13 g/L; Sucrose at a concentration of 22.2 g/L; Citric Acid at a concentration of 3.4 g/L; and Natural Flavors at a concentration of 1.5 g/L.

Accordingly, 500 ml of a liposomal ORS solution is obtained having the following salt concentration:

| | Internal | External | TOTAL (mmol/L) |
|---|---|---|---|
| Na | 15.7 | 12.35 | 28.05 |
| K | 5.04 | 3.62 | 8.66 |
| Cl | 7.84 | 5.61 | 13.45 |
| Cit | 4.90 | 3.02 | 7.92 |
| Glucose | 0 | 16.02 | 16.02 |

This formulation may be suitable for consumption by sportspeople.

Example 8

Process for Preparing the Formulation of the Present Invention with a Percentage Inclusion Ratio of Salts of 56% for High-Performance Sportspeople Stage a A solution of 4.5 L distilled water is prepared with salts at the following concentration:

| | Concentration (mmol/L) | | | | |
|---|---|---|---|---|---|
| | Glucose | Na | K | Cl | Cit |
| Sodium chloride | | 6.01 | | 6.01 | |
| Potassium citrate | | | 3.86 | | 1.29 |
| Sodium citrate | | 6.02 | | | 2.01 |
| Glucose | — | | | | |

Stage b

On the other hand, a solution of phosphatidylinositol in 500 ml of 5% Ethyl alcohol (W/V) is prepared.

Stage c

Liposome formation is induced by injecting the ethanol solution into the aqueous phase while stirring. Here, 15% of the salts are encapsulated. Therefore, the internal and external salt concentrations are the following:

| | Internal | External |
|---|---|---|
| Na | 1.57 | 10.46 |
| K | 0.50 | 3.36 |
| Cl | 0.78 | 5.23 |
| Cit | 0.49 | 2.81 |
| Glucose | 0 | 0 |

Stage d

The 5 Liters of Liposomal ORSs are subjected to a (TUF) tangential ultrafiltration concentration process. This process allows for removing the buffer without eliminating the liposomes and their contents. This process is carried out until the volume is reduced by 10-fold. At the end of the process, 500 ml of liposomal salts having the following concentration is obtained.

| | Internal | External |
|---|---|---|
| Na | 15.7 | 10.46 |
| K | 5.04 | 3.46 |
| Cl | 7.84 | 5.23 |
| Cit | 4.90 | 2.81 |
| Glucose | 0 | 0 |

Stage e

At this stage, buffer substitution is carried out, again with the TUF process. In this case, the total volume is reduced by 10-fold and replaced with an aqueous solution having the following salt concentration:

| | Concentration (mmol/L) |
|---|---|
| Na | 12.56 |
| K | 3.65 |
| Cl | 5.65 |
| Cit | 3.04 |
| Glucose | 0 |

This buffer further contains high fructose corn syrup (55° Brix) at a concentration of 3.22 g/L; Vitamin B1 at a concentration of 0.002 g/L; Vitamin B5 at a concentration of 0.011 g/L; Vitamin B6 at a concentration of 0.011 g/L; Citric Acid at a concentration of 3.6 g/L; and Natural Flavors at a concentration of 1.5 g/L.

Accordingly, 500 ml of a liposomal ORS solution with 50 g/l phosphatidylinositol and the following salt concentration is obtained:

| | Internal | External | TOTAL |
|---|---|---|---|
| Na | 15.7 | 12.35 | 28.05 |
| K | 5.04 | 3.62 | 8.66 |
| Cl | 7.84 | 5.61 | 13.45 |
| Cit | 4.90 | 3.02 | 7.92 |
| Glucose | 0 | 16.02 | 16.02 |

This formulation may be suitable for consumption by high-performance sportspeople.

Example 9

Preclinical Assay of the Rehydration Salt Formulation of the Present Invention

A batch of pediatric liposomal rehydration salts of Example 6 of the present invention as a finished product is compared to commercial product Pedialyte (Abbott Laboratories) taken as reference substance. Said comparison encompassed the development of an osmotic diarrhea model in rats for efficiency evaluation.

Experimental Design:

An osmotic diarrhea experimental model was developed as described in Wapnir et al., 1988, 1991 (Am. J. Clin. Nutr. 1988; 4784-90; J. Pediatr. 1991; 118:S53-61). Four experimental animal groups were used, each consisting of 10 animals (5 male and 5 female animals). Groups 1, 2 and 3 were induced diarrhea by replacing the water for an oral solution of 50% magnesium citrate (USP XXII) for 5 days. Group 4 was not induced diarrhea and was allowed to drink water during said period. Once induction was completed, Group 1 was treated with the test substance; Group 2 was treated with the reference substance; Group 3 received physiological solution; while Group 4 was not treated at all. Body weight, Natremia, Kalemia, and Hematocrit variables were analyzed both during treatment and 12 hours after completion. Young female and male Wistar rats with genetic certification were used. They were divided into subgroups, placed into jails, and identified with a correlative integer number.

The animals were kept under controlled ambient conditions: temperature between 22±3° C., controlled photoperiod (12 hs light/12 hs darkness) and free access to commercial food and water. MicroVENT rack systems provided by Allentown Inc., European Type IIIH (POE GC-065) models, were employed.

Forty (40) animals divided into four experimental groups (each group comprising 5 male and 5 female animals) were used.

Group 1: (5 male and 5 female animals). It was distributed into 2 subgroups: 1-M; 1-F, each consisting of 5 animals of the same sex. These animals were subjected to osmotic diarrhea induction and treated with the test substances.

Group 2: (5 male and 5 female animals). It was distributed into 2 subgroups: 2-M; 2-F, each consisting of 5 animals of the same sex. These animals were subjected to osmotic diarrhea induction and treated with the reference substance.

Group 3: (5 male and 5 female animals). It was distributed into 2 subgroups: 3-M; 3-F, each consisting of 5 animals of the same sex. These animals were subjected to osmotic diarrhea induction and treated with physiological solution.

Group 4: (5 male and 5 female animals). It was distributed into 2 subgroups: 4-M; 4-F, each consisting of 5 animals of the same sex. These animals did not receive any treatment.

Treatment:
Osmotic Diarrhea Induction:

In groups 1, 2, and 3, an osmotic diarrhea experimental model was developed as described in Wapnir et al., 1988, 1991 (Am. J. Clin. Nutr. 1988; 4784-90; J. Pediatr. 1991; 118:S53-61).

Test Substances:
Liposomal Rehydration Salts—Pediatric Formulation of Example 6 of the Present Invention.
Reference Substance:
Rehydration Salts Pedialyte—Pediatric Formulation Manufactured by Abbott Laboratories.
Dosage and Administration:

Groups 1, 2, and 3 were orally administered a total dose of 125 ml/kg/day of the different test substances, distributed in 12 doses at a one-hour-interval between each other. The dose was selected taking into account the dosing instructions of Pedialyte according to which doses of 100 to 150 ml/kg are recommended. The dosage volume of administration was calculated according to the average weight of the male and female rats obtained on Day 5 during the morning, at the time magnesium citrate solution was removed and treatment was initiated, thereby determining differential doses for male and female rats.

The volume corresponding to each dosage was calculated according to the following formula:

$$V\left(\frac{ml}{animal}\right) = \frac{P \times 125}{12 \times 1000}$$

Wherein P is the average weight in grams, either of the male or female rats, as applicable.

Dose administration took place every hour beginning at 9 A.M. on Day 5.

Hematocrit Determination:

Upon the extraction of one drop of blood, a microhematocrit was conducted by using heparinized microtubes. The samples were collected at the following times:

Day 5: 08:00 hs, 12:00 hs, 16:00 hs and 20:00 hs.

The collected samples were also subjected to Natremia and Kalemia determination.

Data Analysis: A comparative analysis of the different formulations was performed through descriptive statistics and two-way analysis of variance (ANOVA), followed by Tukey's multiple comparison test to identify differences between different times. These operations were performed with GraphPad Prism 6.0 software.

Results
Body Mass Recovery:

|  | 1M | | 2M | | 3M | | 4M | |
| --- | --- | --- | --- | --- | --- | --- | --- | --- |
|  | Media | SEM | Media | SEM | Media | SEM | Media | SEM |
| Day 0 | 137.2 | 3.44093 | 137.8 | 2.332381 | 134.2 | 2.2 | 138.4 | 1.805547 |
| Day 1 | 133.8 | 2.61534 | 134 | 2.387467 | 130.6 | 2.357965 | 143.4 | 2.014944 |
| Day 2 | 128.2 | 2.374868 | 128 | 1.760682 | 123.8 | 3.168596 | 143.8 | 1.714643 |
| Day 3 | 122.8 | 2.596151 | 124.4 | 3.091925 | 120.6 | 3.37046 | 146.2 | 2.853069 |
| Day 4 | 112.8 | 4.465423 | 113.8 | 2.477902 | 110.6 | 3.17175 | 149.6 | 2.088061 |
| Day 5 (8 hours) | 108.6 | 3.613863 | 105 | 2.258318 | 103.4 | 2.158703 | 153.4 | 3.249615 |
| Day 5 (12 hours) | 115.8 | 4.140048 | 110.4 | 1.939072 | 109 | 2.50998 | 153.4 | 2.501999 |
| Day 5 (16 hours) | 124.8 | 4.476605 | 115.6 | 1.122497 | 114 | 2.097618 | 155.8 | 2.557342 |
| Day 5 (20 hours) | 133.4 | 4.905099 | 121.4 | 0.6 | 119.6 | 2.249444 | 156.6 | 2.61916 |
| Day 6 | 137.1 | 5.416641 | 125.4 | 1.939072 | 124.4 | 3.043025 | 157.8 | 2.416609 |

|  | 1H | | 2H | | 3H | | 4H | |
| --- | --- | --- | --- | --- | --- | --- | --- | --- |
|  | Media | SEM | Media | SEM | Media | SEM | Media | SEM |
| Day 0 | 118.4 | 0.9273618 | 120.4 | 1.50333 | 120 | 0.9486833 | 119.4 | 2.521904 |
| Day 1 | 112.6 | 1.536229 | 114.6 | 1.469694 | 115 | 1.264911 | 121.2 | 2.709244 |
| Day 2 | 105.6 | 1.28841 | 109.6 | 1.28841 | 107.8 | 2.034699 | 123.8 | 2.61534 |
| Day 3 | 98.8 | 1.714643 | 102 | 1.30384 | 102.8 | 1.907878 | 124.4 | 2.785677 |
| Day 4 | 93.4 | 1.249 | 93.6 | 1.939072 | 96 | 0.8944272 | 126.8 | 2.2 |
| Day 5 (8 hours) | 92.8 | 1.939072 | 89.8 | 1.827567 | 93.2 | 2.437212 | 128.6 | 2.135416 |
| Day 5 (12 hours) | 106.4 | 1.6 | 103 | 2.213594 | 107.8 | 0.9695359 | 127 | 1.949359 |
| Day 5 (16 hours) | 112.6 | 1.4 | 101.6 | 1.860107 | 108.6 | 1.886796 | 126 | 2.073644 |

| | | | | | | | | |
|---|---|---|---|---|---|---|---|---|
| Day 5 (20 hours) | 116.6 | 1.886796 | 102.6 | 1.469694 | 113.2 | 1.157584 | 123.4 | 2.420743 |
| Day 6 | 118.6 | 2.420743 | 102.6 | 1.16619 | 110 | 1.449138 | 126.8 | 2.332381 |

Figure 4:
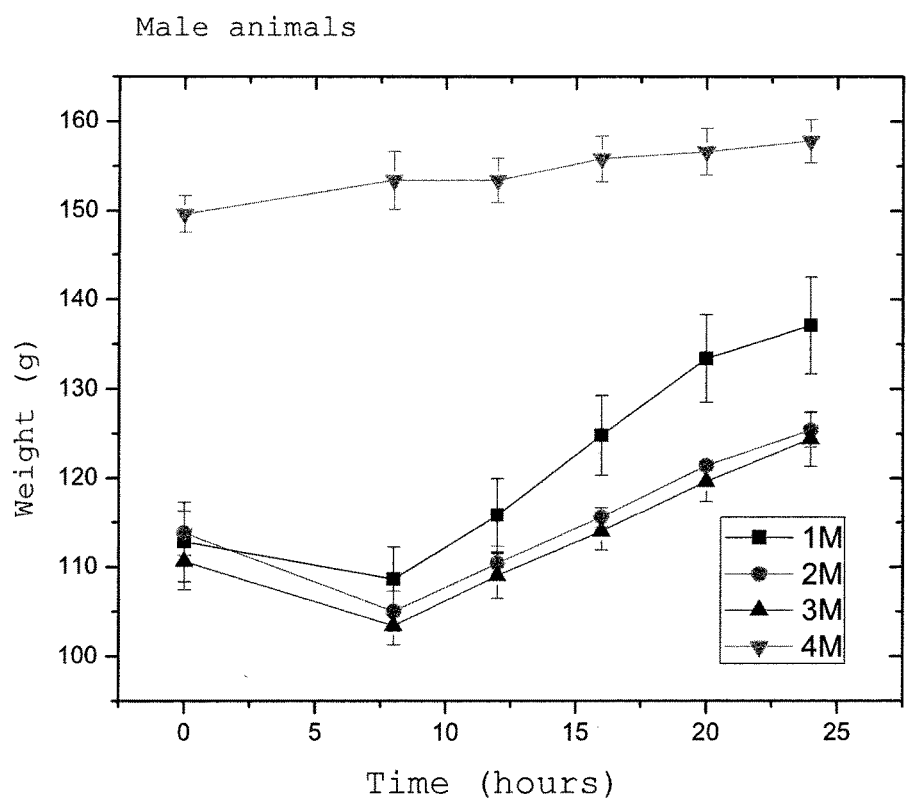
FIG. 4 represents the evolution of body mass in male animals according to Example 9.
Figure 5:
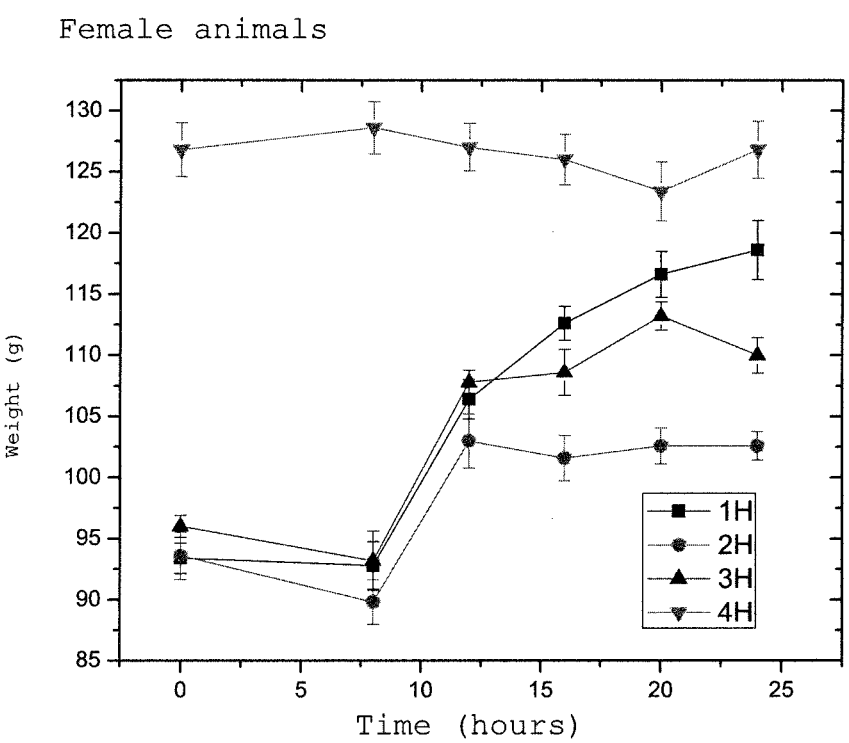
FIG. 5 represents the evolution of body mass in female animals according to Example 9.

See FIGS. 4 and 5
Hematocrit Concentration:

| | 1M | | 2M | | 3M | | 4M | |
|---|---|---|---|---|---|---|---|---|
| | Media | SEM | Media | SEM | Media | SEM | Media | SEM |
| Day 5 (8 hours) | 54.6 | 1.029563 | 54 | 0.83666 | 52.4 | 0.4 | 44.4 | 0.6 |
| Day 5 (12 hours) | 48.6 | 0.4 | 50.8 | 0.374166 | 50.6 | 0.6 | 46.2 | 0.583095 |
| Day 5 (16 hours) | 46.6 | 0.4 | 49.2 | 0.374166 | 48.4 | 0.509902 | 45 | 0.316228 |
| Day 5 (20 hours) | 45 | 0.547723 | 48.4 | 0.678233 | 45.2 | 0.860233 | 43 | 0.632456 |
| Day 6 | 44.4 | 1.32665 | 48 | 1.516575 | 46.6 | 2.249444 | 44 | 0.948683 |

| | 1H | | 2H | | 3H | | 4H | |
|---|---|---|---|---|---|---|---|---|
| | Media | SEM | Media | SEM | Media | SEM | Media | SEM |
| Day 5 (8 hours) | 55.6 | 1.32665 | 54.8 | 0.734847 | 53 | 0.547723 | 46.6 | 0.4 |
| Day 5 (12 hours) | 47.2 | 0.2 | 50.4 | 0.678233 | 50.6 | 0.509902 | 47.2 | 0.583095 |
| Day 5 (16 hours) | 45.8 | 0.2 | 49.6 | 0.6 | 47.8 | 0.2 | 45.4 | 0.979796 |
| Day 5 (20 hours) | 44.4 | 0.509902 | 47.8 | 0.374166 | 45.8 | 1.2 | 44.8 | 0.860233 |
| Day 6 | 43.2 | 0.374166 | 45.4 | 1.630951 | 41.4 | 1.860107 | 42.2 | 1.772004 |

Figure 6:
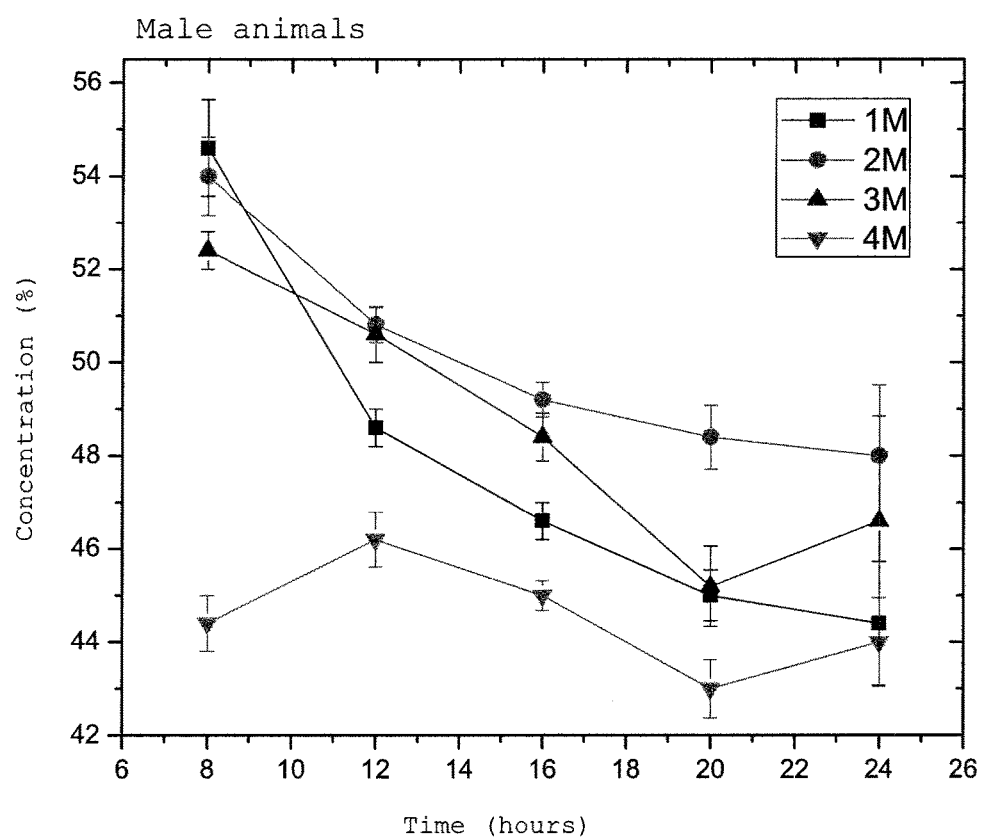
FIG. 6 represents the evolution of hematocrit concentration in male animals according to Example 9.
Figure 7:
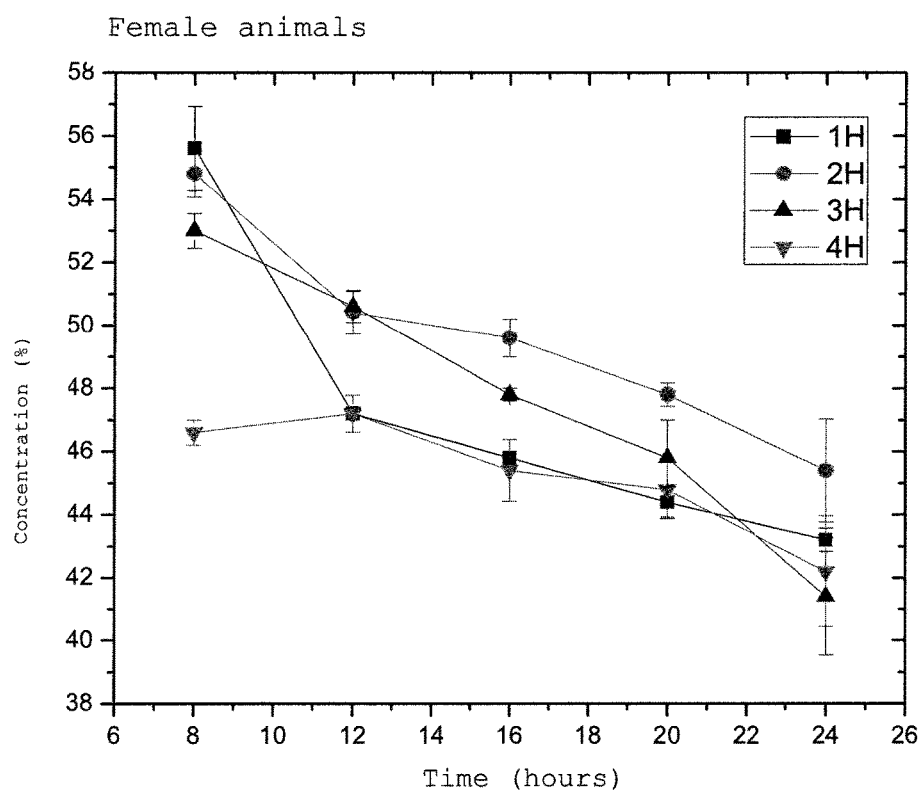
FIG. 7 represents the evolution of hematocrit concentration in female animals according to Example 9.

See FIGS. 6 and 7
Natremia (mmol/L):

| | 1M | | 2M | | 3M | | 4M | |
|---|---|---|---|---|---|---|---|---|
| | Media | SEM | Media | SEM | Media | SEM | Media | SEM |
| Day 5 (8 hours) | 200.8 | 3.624914 | 194.6 | 5.1049 | 193 | 4.312772 | 175 | 1.341641 |
| Day 5 (12 hours) | 178.4 | 1.32665 | 191.2 | 1.655295 | 192.4 | 3.893584 | 169.4 | 3.059412 |
| Day 5 (16 hours) | 175.2 | 1.655295 | 190.4 | 1.363818 | 192 | 1.923538 | 173.4 | 2.420743 |
| Day 5 (20 hours) | 175.6 | 1.50333 | 187.2 | 0.7348469 | 189.2 | 1.933908 | 173.2 | 1.496663 |
| Day 6 | 175.2 | 1.593738 | 185.2 | 1.714643 | 187 | 1.48324 | 174.4 | 2.088061 |

| | 1H | | 2H | | 3H | | 4H | |
|---|---|---|---|---|---|---|---|---|
| | Media | SEM | Media | SEM | Media | SEM | Media | SEM |
| Day 5 (8 hours) | 190.2 | 4.97393 | 194.8 | 3.15278 | 185.6 | 1.8868 | 175.2 | 1.06771 |
| Day 5 (12 hours) | 173.6 | 1.46969 | 192.4 | 2.01494 | 180.2 | 1.06771 | 172.6 | 1.36382 |
| Day 5 (16 hours) | 169.8 | 1.35647 | 189.4 | 2.37907 | 177.2 | 1.15758 | 171.2 | 3.77359 |
| Day 5 (20 hours) | 173.2 | 1.35647 | 188.4 | 1.43527 | 172 | 1.09545 | 174.4 | 2.37907 |
| Day 6 | 171.4 | 3.58608 | 185.2 | 1.88149 | 171.8 | 1.98494 | 174.6 | 1.20831 |

Figure 8:
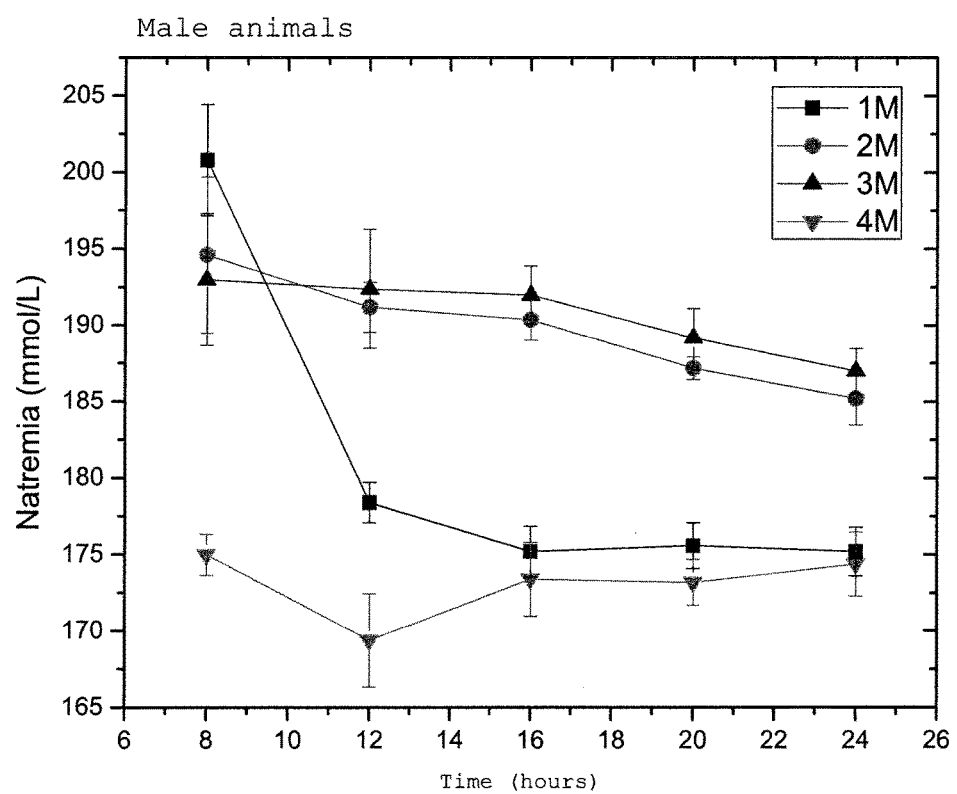
FIG. 8 represents the evolution of sodium concentration (Natremia) (mmol/L) in male animals according to Example 9.
Figure 9:
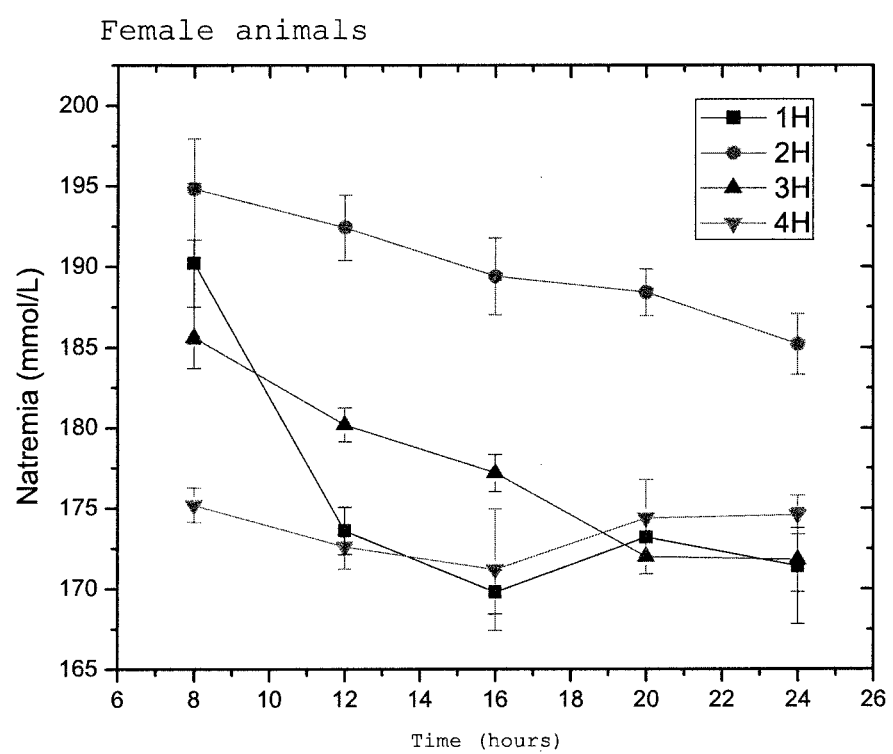
FIG. 9 represents the evolution of sodium concentration (Natremia) (mmol/L) in female animals according to Example 9.
Figure 10:
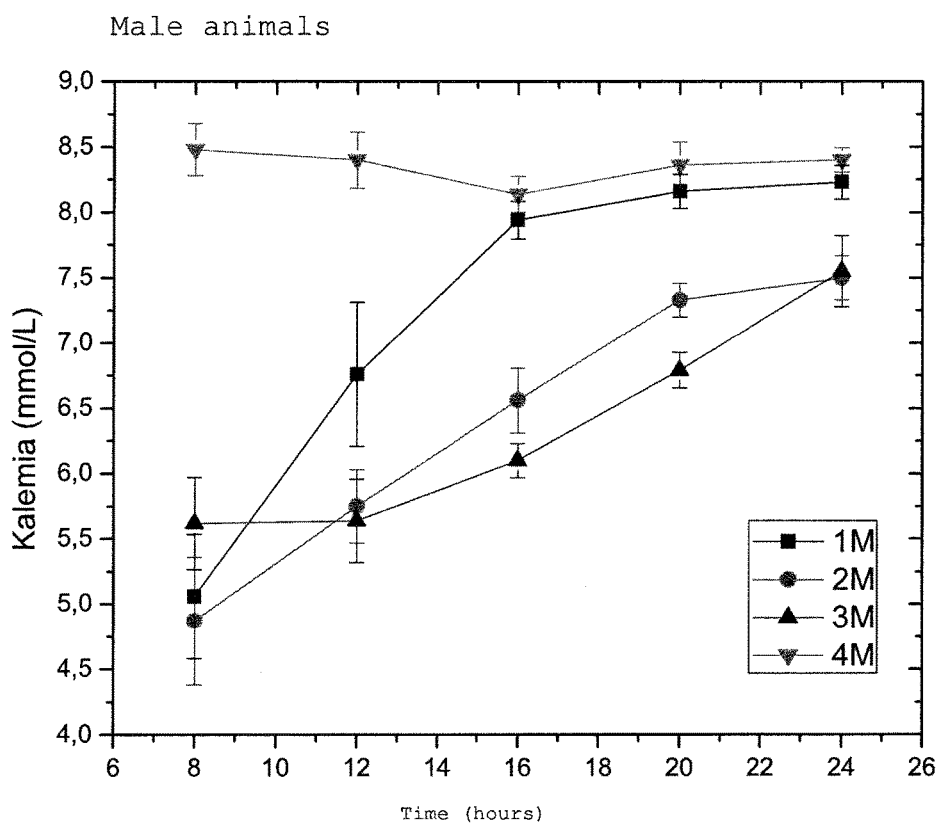
FIG. 10 represents the evolution of potassium concentration (Kalemia) (mmol/L) in male animals according to Example 9.
Figure 11:
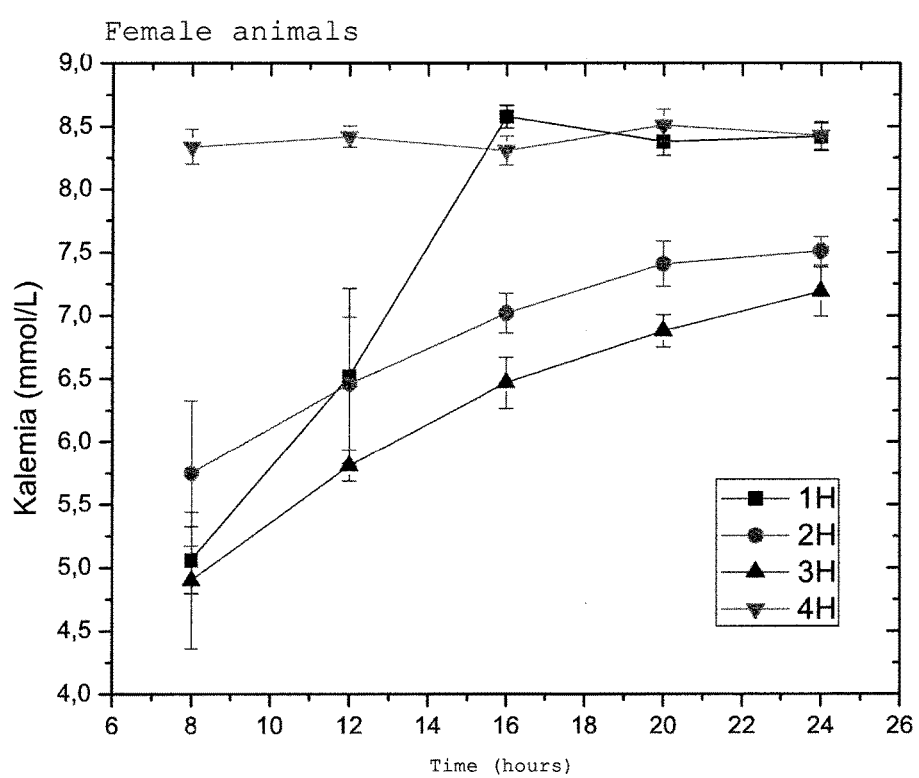
FIG. 11 represents the evolution of potassium concentration (Kalemia) (mmol/L) in female animals according to Example 9.

See FIGS. 8 and 9
Kalemia (mmol/L):

| | 1M | | 2M | | 3M | | 4M | |
|---|---|---|---|---|---|---|---|---|
| | Media | SEM | Media | SEM | Media | SEM | Media | SEM |
| Day 5 (8 hours) | 5.06 | 0.478121 | 4.87 | 0.4895406 | 5.62 | 0.3527038 | 8.48 | 0.2009974 |
| Day 5 (12 hours) | 6.76 | 0.552811 | 5.75 | 0.2792848 | 5.64 | 0.3187475 | 8.4 | 0.2167949 |
| Day 5 (16 hours) | 7.94 | 0.143527 | 6.56 | 0.2466778 | 6.1 | 0.1294218 | 8.139 | 0.1363817 |
| Day 5 (20 hours) | 8.16 | 0.129807 | 7.33 | 0.1299999 | 6.79 | 0.1372953 | 8.36 | 0.1784657 |
| Day 6 | 8.23 | 0.128062 | 7.5 | 0.1695582 | 7.55 | 0.2720294 | 8.4 | 0.0935415 |

| | 1H | | 2H | | 3H | | 4H | |
|---|---|---|---|---|---|---|---|---|
| | Media | SEM | Media | SEM | Media | SEM | Media | SEM |
| Day 5 (8 hours) | 5.06 | 0.26429 | 5.75 | 0.57619 | 4.9 | 0.54106 | 8.34 | 0.14 |
| Day 5 (12 hours) | 6.52 | 0.69401 | 6.46 | 0.52617 | 5.81 | 0.12288 | 8.42 | 0.08456 |
| Day 5 (16 hours) | 8.58 | 0.09028 | 7.02 | 0.157 | 6.47 | 0.20224 | 8.309 | 0.11662 |

| | | | | | | | | |
|---|---|---|---|---|---|---|---|---|
| Day 5 (20 hours) | 8.38 | 0.10794 | 7.41 | 0.17986 | 6.88 | 0.12806 | 8.51 | 0.12787 |
| Day 6 | 8.42 | 0.10794 | 7.51 | 0.11225 | 7.19 | 0.19261 | 8.43 | 0.11023 |

CONCLUSIONS

The osmotic diarrhea model was developed as described in the literature, resulting in significant weight reduction and hematocrit increase due to dehydration.

During dehydration process due to fecal excretion, significant loss of extracellular fluid is produced. Sodium concentration in this fluid is about 30 times higher compared to potassium concentration. During the process of fluid loss, significant loss of solutes is also observed, including sodium and potassium ions, responsible for regulating liquid restitution in the body. However, the percentage of potassium loss is higher than that corresponding to sodium. In addition to liquid reduction, this makes the initial dehydration condition show plasma sodium concentration values higher than those belonging to animals that did not experienced dehydration, and plasma potassium concentration values lower than those of non-dehydrated animals.

The results obtained from the body mass analysis indicated that, as a consequence of diarrhea induction, all the experimental groups by the time treatment was initiated had lost about 20% of their body mass. Thereafter, comparative results showed a significant difference between weight regain in the group treated with the formulation of Example 6 of the present invention and the group treated with Pedialyte®. Both in male and female rats after 24 hours of treatment, the formulation of the present invention induced recovery of average body mass in the experimental group.

Hematocrit is the percent of the total volume of whole blood that is composed of red blood cells. Hematocrit loss during dehydration due to fecal excretion is negligible. This implies that the reduction of plasma extracellular fluid makes hematocrit increase.

On the basis of the condition at the time treatment was initiated, it is possible to see that all the induced groups have a hematocrit level higher than 50%, where all normal values always range from 40% to 50%. The treatment results indicate that recovery in the hematocrit level in the group treated with the formulation of the present invention was significantly faster than that achieved by Pedialyte®. In male rats, normal level was achieved after 24 hours of treatment, whereas in female rats the action was much more effective, the normal level being recovered after 8 hours of treatment.

Natremia and Kalemia analyses are highly influenced by extracellular fluid recovery. Reduction in sodium concentration in all the experimental groups does not mean there is cation loss, but a reduction in cation concentration. This means the body absorbs sodium and recovers a higher liquid percentage; thus, its concentration diminishes. The experimental results revealed that both in male and female rats, the recovery rate of normal sodium and potassium levels was significantly higher for the formulation of the present invention compared to Pedialyte®.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A method for preparing a liposomal rehydration salt formulation, comprising:
    a. preparing an aqueous phase or buffer comprising sodium chloride, potassium citrate, and sodium citrate dissolved in distilled water, wherein the aqueous phase or buffer comprises sodium chloride at a concentration of about 0.35 grams/liter (g/l) to 1.17 g/l; potassium citrate at a concentration of about 0.31 g/l to 2.14 g/l; sodium citrate at a concentration of about 0.52 g/l to 1.29 g/l; and distilled water;
    b. separately preparing an alcohol phase by dissolving a phospholipid in ethanol at a concentration of about 25.0 g/l to 60 g/l and an antioxidant at a concentration of 2.0 g/l to 5.0 g/l;
    c. inducing formation of liposomes by injecting the alcohol phase into the aqueous phase at room temperature, while mixing to form a liposomal dispersion;
    d. removing up to 90% volume of the previous liposomal dispersion and aqueous phase solutes that are not trapped in the liposomes using tangential flow ultrafiltration; and
    e. filtering the solution obtained in step d using tangential flow ultrafiltration while feeding the solution at a speed equal to the permeation speed with an aqueous saline solution comprising a sodium concentration of 0.28 g/l to 1.15 g/l; a potassium concentration of 0.12 g/l to 0.55 g/l; a chloride concentration of 0.18 g/l to 1.42 g/l; a citrate concentration of 0.58 g/l to 1.92 g/l; and a carbohydrate, and maintaining the liposomes and the contents therein and forming the liposomal rehydration salt formulation comprising phospholipids, salts, and wherein the salts comprise sodium chloride at a concentration of about 0.7 g/l to 2.8 g/l, potassium citrate at a concentration of about 0.8 g/l to 2.5 g/l, sodium citrate at a concentration of about 0.5 g/l to 2.9 g/l, an antioxidant at a concentration of about 2.0 g/l to 5.0 g/l, a carbohydrate, water, and a percentage inclusion ratio of salts (salts retained within total salts/liposomes) of at least 50% and wherein the formulation has an osmotic concentration lower than 190 mosm/l, and the liposomes comprising a particle diameter from about 225 nm to 450 nm.

2. The method according to claim 1, wherein in step "a" the phospholipids are selected from the group consisting of phosphatidylcholines (PCs), phosphatidylserines (PSs), phosphatidylethanolamines (PEs), phosphatidylglycerols (PGs), phosphatidylinositols (PIs), phosphatidic acids (PAs), and mixtures thereof.

3. The method according to claim 1, wherein the aqueous phase to alcohol phase volume ratio in step c is at least 10:1.

4. The method according to claim 1, wherein the aqueous phase to alcohol phase volume ratio in step c is at least 10:0.5.

5. The method according to claim 1, wherein the aqueous phase to alcohol phase volume ratio in step c is at least 10:0.4.

6. The method according to claim 1, wherein the alcohol phase is added in a perpendicular flow process to the aqueous phase by perpendicular coupling to the flow of the aqueous phase with a linear velocity ratio of the alcohol phase to the aqueous phase of no more than 1/200.

* * * * *

UNITED STATES PATENT AND TRADEMARK OFFICE
CERTIFICATE OF CORRECTION

PATENT NO. : 10,238,687 B2
APPLICATION NO. : 15/723228
DATED : March 26, 2019
INVENTOR(S) : Nicastro et al.

Page 1 of 1

It is certified that error appears in the above-identified patent and that said Letters Patent is hereby corrected as shown below:

On the Title Page

Related U.S. Application Data (Item (63)):

Delete:
"Continuation of application No. 15/111,485, filed as application No. PCT/ES2015/070003 on Jan. 7, 2015."

Insert:
-- Continuation of application No. 15/111,485 filed on July 14, 2016, which is a 371 of PCT/ES2015/070003 filed on January 7, 2015. --

Signed and Sealed this
Twenty-first Day of May, 2019

Andrei Iancu
*Director of the United States Patent and Trademark Office*